United States Patent [19]

Bille et al.

[11] Patent Number: 4,764,930
[45] Date of Patent: Aug. 16, 1988

[54] MULTIWAVELENGTH LASER SOURCE

[75] Inventors: Josef F. Bille, Solana Beach; Stuart I. Brown, La Jolla, both of Calif.

[73] Assignee: Intelligent Surgical Lasers, La Jolla, Calif.

[21] Appl. No.: 148,866

[22] Filed: Jan. 27, 1988

[51] Int. Cl.$^4$ .................................................. H01S 3/10
[52] U.S. Cl. ........................................ 372/23; 372/25; 372/75; 372/12
[58] Field of Search ..................... 372/25, 23, 200, 20, 372/75, 69, 70, 18, 12

[56] References Cited

U.S. PATENT DOCUMENTS

| | | | |
|---|---|---|---|
| 4,053,845 | 10/1977 | Gould | 330/4.3 |
| B1 4,053,845 | 4/1987 | Gould | 330/4.3 |
| 4,161,436 | 7/1979 | Gould | 204/157.1 R |
| 4,205,278 | 5/1980 | George et al. | 372/69 |
| 4,503,854 | 3/1985 | Jako | 128/303.1 |
| 4,517,980 | 5/1985 | Tagnon | 128/395 |
| 4,561,436 | 12/1985 | Munnerlyn | 128/303.1 |
| 4,601,288 | 7/1986 | Myers | 128/303.1 |
| 4,612,641 | 9/1986 | Corkum | 372/25 |
| 4,622,967 | 11/1986 | Schachar | 128/303.15 |
| 4,638,800 | 1/1987 | Michel | 128/303.1 |
| 4,665,913 | 5/1987 | L'Esperance, Jr. | 128/303.1 |
| 4,669,466 | 6/1987 | L'Esperance | 128/303.1 |
| 4,685,107 | 8/1987 | Kafka et al. | 372/25 |
| 4,704,583 | 11/1987 | Gould | 330/4.3 |

OTHER PUBLICATIONS

"FM-Laser Operation for the Nd:YAG Laser," by Kuizenga et al., IEEE Journal of Quantum Electronics, Nov. 1970.

"Laser Interactions with the Cornea," by Krauss et al., Survey of Ophthalmology, Jul.-Aug. 1986.

"Noncontact Trephination of the Cornea Using a Pulsed Hydrogen Fluoride Laser," Loertscher et al., American Journal of Ophthalmology, Nov. 1987.

"Room-Temperature 2 um HO:YAG and 3 um ER:YAG Lasers," by Huber et al., to be published in Journal de Physique.

"Defects in the Optical Synthesis," publication and date unknown.

Primary Examiner—Léon Scott, Jr.
Attorney, Agent, or Firm—Workman, Nydegger & Jensen

[57] ABSTRACT

A multiwavelength laser source for providing a plurality of pulsed laser beams comprises a plurality of laser diodes optically connected with an oscillator to establish a beam of pulses of monochromatic light. A dispersion line for spreading wavelengths in each pulse optically connects the oscillator to a regenerative amplifier. An electro-optical crystal in the regenerative amplifier establishes the repetition rate of pulses in the laser beam and a pulse compressor is optically connected to the regenerative amplifier to establish the duration of each pulse. The laser source may also include a frequency doubler which is optically connected to the output of the pulse compressor to split the laser beam into components having different wavelengths.

22 Claims, 2 Drawing Sheets

MULTIWAVELENGTH LASER SOURCE

BACKGROUND OF THE INVENTION

This invention relates generally to multiwavelength laser sources. More particularly, this invention relates to a laser source which establishes a multiwavelength beam of laser pulses in which the duration of each pulse is extremely short and in which the repetition rate for pulses in a given unit of time is very high. This invention is particularly, but not exclusively, useful for ophthalmic surgery.

DISCUSSION OF THE PRIOR ART

Lasers have been used for various purposes with profound results for many years. Although the theories of this technology are complicated and highly sophisticated, a general understanding of several basic notions underlying the technical complications is sufficient to appreciate the contributions made by the present invention.

As is well known to the skilled artisan, laser beams are intense light-frequency radiations of highly collimated coherent monochromatic light. Further, it is known that laser beams can be generated by the proper excitation of selected active media, including gases or crystals, in a process commonly referred to as "pumping." Just how the resultant radiated light in a laser beam is constituted is the concern of the present invention.

The most important parameters for understanding the basic uses of laser technology are the wavelength of the radiations, the duration of these radiations and their intensity. As will be readily appreciated, variations in these parameters are made to optimize the efficacy of the laser beam for the particular purpose it is being employed. When used for ophthalmic surgery, several specific considerations become important. Primarily, the concern in ophthalmic surgery, like that in other surgical applications, centers on factors which enhance the ability to perform the required surgical operation while minimizing trauma to the tissue. A thorough discussion of this matter is set forth in an article entitled "Laser Interactions with the Cornea" by Joel M. Krauss et al. and published in Survey of Ophthalmology, Volume 31, Number 1, July–August 1986. Not surprisingly, the Krauss article and other references believe the constituency of the laser beam significantly determines its efficacy for ophthalmic surgery. With this in mind, a basic understanding of laser beams is helpful.

Many articles have been written on the importance of a laser beam's wavelength. As is well known, the interaction between a laser beam and the human tissue on which it is incident is wavelength dependent. This is so because different tissues have different absorption characteristics. Consequently, laser sources must be carefully selected depending on the purpose for which they are to be used. Since each active medium has its characteristic wavelength, any variation in this parameter is essentially a matter of choice. This is not so with the other important variables dealing with laser beam intensity and duration.

Insofar as duration is concerned, laser beams can be generally categorized as either continuous beams or pulsed beams. It happens that pulsed laser beams are more effective than are the continuous laser beams for most medical procedures. With the continuous beam, the duration of the laser beam lasts as long as the beam is turned on. On the other hand, the duration of a pulsed beam is more properly considered as referring to the sum of the durations of individual pulses. Presently, pulses in the picosecond range (1 ps = 1 picosecond = $10^{-12}$ seconds) are attainable but not practically useable for ophthalmic surgery. Instead, pulses in the nanosecond range are typically used (1 ns = 1 nanosecond = $10^{-9}$ seconds).

Typically, in surgical procedures when a pulsed beam is used, groups of pulses are employed in bursts. Unlike such structure for a laser beam, in the contemplation of the present invention, a pulsed laser beam is established which is really quasi-continuous in nature. Thus, the laser beam established by the laser source of the present invention establishes a continuous train of pulses having equal energy and time duration and a very high repetition rate.

As stated above, wavelength, duration and intensity are all important parameters for describing the characteristics of a laser beam. Not unexpectedly, these parameters are interrelated. Specifically, these variables are related to each other according to the expressions:

$P = E/t$, and $E = nhc/\lambda$; where

P is intensity or cutting power, E is energy, t is pulse duration, h is Planck's constant, c is the speed of light, $\lambda$ is wavelength and n is the number of photons per pulse.

It will be seen from the above expressions that energy (E) is inversely proportional to the wavelength of the light ($\lambda$). Also, from the above expression for intensity (P), it will be seen that if the duration (t) of each pulse can be effectively reduced, the intensity or cutting power of the laser beam can be maintained even though pulses of lower energy having longer wavelengths are used. It happens that several procedures of ophthalmic surgery are effective only when longer wavelength laser pulses are employed. Consequently, the ability to control duration (t) becomes extremely important.

Presently used laser surgical procedures recognize that it is the energy of a laser beam, i.e. the number of photons in the beam or pulse, which determines the effect the beam has on tissue. This effect can be generally described as either thermal, or electromechanical or a combination thereof. As is well known, although the effect should be highly localized to achieve an efficacious result, the relatively high energy levels of presently used laser beams invariably cause unnecessary damage to peripheral tissue.

The present invention recognizes that both the cutting of tissue and changes in the elastic properties of tissue can be achieved with an electric field effect which obviates the adverse peripheral consequences of the thermal and electromechanical effects mentioned above. While a complete disclosure of the electric field effect is beyond the scope of this application, it is deemed important to note that, unlike the thermal and electromechanical effects, this effect does not depend on the energy in a laser beam. Instead, it depends on the beam's intensity, i.e. the number of photons striking the target area in a given unit of time. Thus, whenever the electric field effect is to be used to alter tissue structure, the goal is to maintain a beam intensity which is sufficient to accomplish this end while reducing the beam's energy level to a point where unwanted thermal and electromechanical effects are confined to a highly localized area. From the expression $P=E/t$, however, it will be understood that energy and intensity are proportional. Therefore, intensity can be generally maintained whenever energy is reduced only if pulse duration (t) is also reduced.

In accordance with the present invention, the pulse durations of a laser beam are greatly reduced from those presently achieved in other laser beams by today's state-of-the-art technology. The well known excimer laser, for instance, typically produces pulses of 10 nanosecond duration. The present invention, on the other hand, envisions pulses of one or only a few picosecond duration. This is a reduction in pulse duration by a factor of approximately ten thousand. Also, in order to reduce the adverse effects to peripheral tissue caused by thermal or electromechanical alterations, the present invention envisions energy levels in each pulse which are a factor of one thousand less than the levels attained in presently used laser beams. The result is a beam which has an intensity level that is approximately ten times higher than the intensity levels attained in commonly used laser beams at this time. Accordingly, the electric field effect is enhanced and the thermal and electromechanical effects are minimized.

Another factor which figures into the efficacy of the present invention is focal area. Again reference is made to the popular excimer laser which affects areas approximately one hundred microns in diameter. In stark contrast to such focal areas, the present invention envisions affecting areas approximately one micron in diameter. Additionally, it will be appreciated that, although short duration pulses are used, the total power available to cut the tissue will be the sum of the cutting powers for each pulse. Therefore, it follows that repetition rate is also a major consideration in developing an effective ophthalmic laser. Accordingly, rather than hit the target area with a burst of energy over a large target area, as has been the practice, it is the purpose of the present invention to affect many small target areas with sufficient intensity to effectively change the photoelastic properties of the tissue. In this way, the present invention accomplishes the same desirable effect as the high energy beam without suffering the adverse effects on peripheral tissue. Briefly, the present invention is intended to produce a quasi-continuous beam of high-intensity low-energy pulses which can be aimed at different selected target areas at a very high repetition rate.

In light of the above, recall that the wavelength of the light in a laser beam is dependent on the active medium used and that different wavelengths have different effects on human tissue. Accordingly, it is important to select an active medium which can be based to produce light having the desired wavelength. Importantly, however, the combined effect of these variables will determine whether the tissue is affected thermally or electromechanically to achieve the desired result. Thus, the ability to control pulse duration and intensity is crucial.

The present invention recognizes that the most effective and efficacious way in which to cut eye tissue is by a procedure known in the art as photoablation. With this procedure, pulses preferably have very short durations, e.g. 1–40 picoseconds, with high repetition rates, e.g. in a range of ten thousand (10,000) to one million (1,000,000) pulses per second. Further, the present invention recognizes that the above-mentioned electric field effect can be used either to mechanically sever the bonds between cell tissue to create an incision or to alter the elastic properties of the cells and change their interactive bonds with other cells. The particular result obtained depends on the selection of wavelength. With this in mind, the present invention recognizes that, for specific applications in ophthalmic surgery, external ablation (mechanical severance) can be accomplished on corneal tissue with a laser beam having a wavelength of 2.94 microns and that internal ablation (elastic alteration) can be accomplished on corneal tissue with wavelengths of 1.06 and 0.532 microns. The intention of the present invention is to incorporate a crystal capable of producing a multiwavelength beam useful for electric field effect on corneal tissue having all these wavelengths. This, however, cannot be construed as a limitation for the present invention. Indeed, the present invention will be useful in angioplasty procedures and neurosurgical procedures depending upon the active medium chosen. Accordingly, it is to be appreciated that any active medium can be used with the present invention depending only on the procedural requirements and the consequent efficacious laser wavelengths.

Besides applications in ophthalmic surgery, the new laser source has many other uses in medical surgery. Modern optical systems and fiber-optic catheters can be configured to deliver laser light to virtually anywhere in the body. For example, in laser angiosurgery, laser light can be passed through an optical fiber to clear plaque from blocked arteries. Initially, CW-Argon ion and Nd:YAG lasers were used in experimental trials for angiosurgery. Recently, the pulsed ultraviolet radiation of excimer lasers has been studied which allows for the destruction of calcified plaques. The accompanying problem of blood vessel wall perforation, however, has not been satisfactorily solved until now. The laser source described in this invention applied through an imaging optical fiber bundle will allow for a substantially improved control of the photoablation process.

Similarly, in laser lithotripsy, which is proving to be an effective substitute for acoustic techniques in many cases, kidney or gall bladder stones can be destroyed with greatly enhanced precision.

In neurosurgery, a new laser source according to the present invention will spare more of the surrounding delicate tissue than possible until now. In ear surgery, the finely focused laser beam can be used to selectively vaporize material to free the stapes, after which they can be gently lifted out and replaced with artificial parts. The procedure reduces bleeding and greatly reduces damage to the delicate inner ear. Recovery will be more confortable and rapid.

Among many potential industrial applications, the new laser source provides a fast and precise tool for cleaning and etching of VLSI microstructures. Many other applications in micromachining are feasible.

In light of the above, it is an object of the present invention to provide a pulsed laser light source which provides very short duration pulses at extremely high repetition rates. It is another object of the present invention to provide a laser source in which both the pulse duration and the repetition rate can be varied. Yet another object of the present invention is to provide a laser source which is compatible with various active media to obtain useful wavelengths which are efficacious for the desired procedure. Still another object of the present invention is to provide a multiwavelength laser system which is relatively easy to manufacture and which is cost effective.

SUMMARY OF THE INVENTION

A preferred embodiment of the novel multiwavelength laser source, according to the present invention, includes a plurality of laser diodes which provide input to a laser oscillator. The oscillator includes an active medium, such as a crystal, which is pumped by light from the laser diodes to create a laser beam having predetermined wavelengths. In accordance with the present invention a YSGG:Cr:Nd:Er crystal is preferably used to produce a laser beam having desired multiwavelengths. An acousto-optic mode locker is incorporated into the oscillator to divide light radiating along the optical axis of the oscillator into pulses.

A dispersion line is optically connected to the output of the oscillator for the purpose of spreading wavelengths within the pulses of the laser beam. Preferably, this dispersion line comprises a monomode optical fiber which is approximately 20 meters in length. The pulses emanating from the dispersion line are optically directed toward a regenerative amplifier where pulses in the laser beam are amplified. Subsequently, an electro-optical crystal within the regenerative amplifier is selectively activated to vary the plane of polarization of the pulses. With a first change in the plane of polarization by the electro-optical crystal, the pulses are captured in the amplifier and are amplified in the regenerative amplifier by their interaction with a laser pumping chamber. With a sequential change in the plane of polarization by the electro-optical crystal, amplified pulses are diverted from the regenerative amplifier and directed toward a pulse compressor.

The pulse compressor comprises a grating optically connected with a corner cube that is moveable relative to the grating. According to the distance of the corner cube from the grating, the duration of each pulse can be established. A frequency doubler may also be incorporated in cooperative association with the pulse compressor to provide a pulsed laser beam having half the wavelength of the pulsed laser beam generated at the oscillator.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENT

Figure 1:
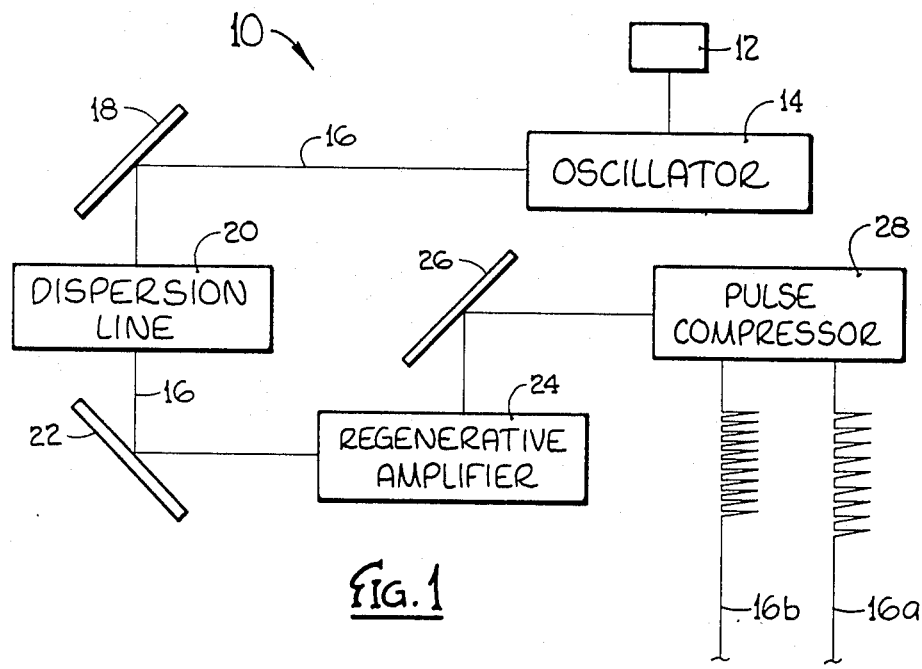
FIG. 1 is a block diagram showing the operative connection of components of the laser source according to the present invention.

Referring initially to FIG. 1, it will be seen that the multiwavelength laser source in accordance with the present invention is generally designated 10 and comprises several components. Specifically, multiwavelength laser source 10 includes an array 12 of laser diodes which provide the optical input to oscillator 14 necessary to excite the active medium. The result is a mode locked pulsed laser beam 16 as an output from oscillator 14. Pulsed laser beam 16 is directed by turning mirror 18 into a dispersion line 20 where the wavelengths of light in the pulses of beam 16 are spread. As beam 16 emerges from dispersion line 20 it is directed by turning mirror 22 toward regenerative amplifier 24 where the individual pulses in beam 16 are amplified. Additionally, in a manner to be subsequently discussed, the repetition rate of pulses in beam 16 for any given period of time is established within regenerative amplifier 24. Upon being diverted from regenerative amplifier 24, laser beam 16 is directed by turning mirror 26 toward pulse compressor 28 where the duration of each pulse in laser beam 16 is established. As shown in FIG. 1, pulse compressor 28 has means to selectively create pulsed laser beams 16a and 16b having different wavelengths. A greater appreciation of the laser source 10 of the present invention will be obtained by reference to each component individually.

Figure 2:
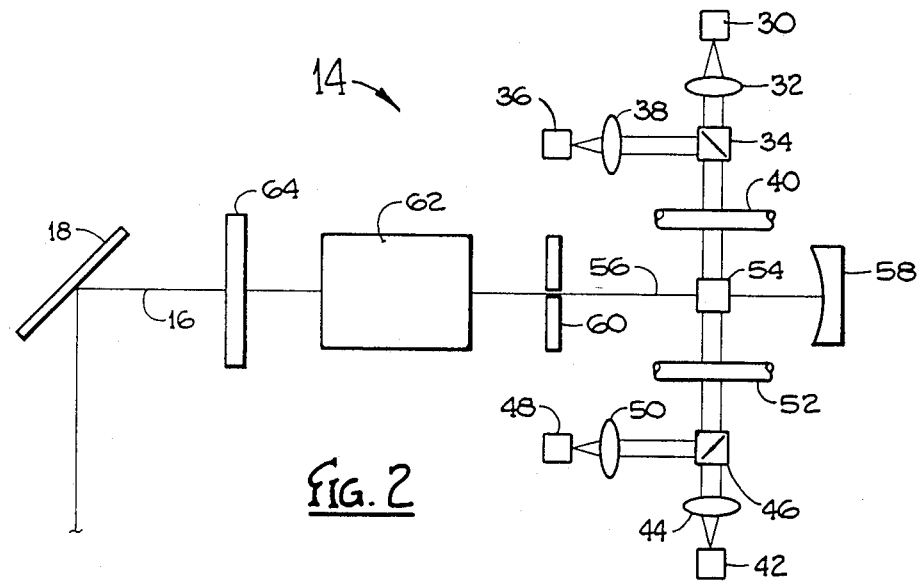
FIG. 2 is a schematic diagram of the oscillator of the present invention.

Referring to FIG. 2, it will be seen that array 12 of oscillator 14 includes a laser diode 30 which has its light directed through collimator lens 32 into beam splitter 34. Likewise, a laser diode 36 is incorporated with its light beam directed through collimator lens 38 into beam splitter 34. At beam splitter 34, light from laser diodes 30 and 36 are combined and directed through cylindrical lens 40. FIG. 2 also shows that additional structure is provided with laser diode 42 directing its light through collimator lens 44 and into beam splitter 46 while laser diode 48 directs its light through collimator lens 50 and into beam splitter 46. At beam splitter 46, the light from laser diodes 42 and 48 are combined and passed through cylindrical lens 52. As shown in FIG. 2, the light passing through cylindrical lens 40 and the light passing through cylindrical lens 52 are both incident on crystal 54. The skilled artisan will recognize this combination of laser diodes, beam splitters and cylindrical lenses as a pumping chamber. Preferably laser diodes 30, 36, 42 and 48 are of the type SLD 2460.

In accordance with the present invention, the active medium is a crystal 54 which is preferably a YSGG:Cr:Nd:Er crystal. It is to be understood, however, that the particular YSGG:Cr:Nd:Er crystal 54 is only exemplary. Indeed, any active medium may be used within the spirit of the present invention to provide a laser beam which will have the desired characteristics. It is known that upon being properly pumped by peripheral laser sources such as laser diodes 30, 36, 42 and 48 that a YSGG:Cr:Nd:Er crystal 54 will generate laser beams having wavelengths of 1.06 microns and 2.94 microns. For purposes to be subsequently discussed, a portion of the 1.06 micron wavelength laser beam can be subsequently diverted through a frequency doubler to establish a laser beam having a wavelength of 0.532 microns. Thus, in accordance with the present invention, most active media, such as crystal 54 described here, will provide a laser source 10 which is capable of generating laser beams of three different wavelengths. For reasons previously stated, this adds versatility to the system and allows its use in a wider variety of procedures.

Still referring to FIG. 2, it can be seen that portions of the laser light generated by pumping crystal 54 will radiate along optical axis 56. Further, it will be appreciated by the skilled artisan that laser light radiating along optical axis 56 will reciprocate along axis 56 between a curved 100% mirror 58 and a flat 98% mirror 64, through an aperture 60 and through an acousto-optic mode locker 62. The operation of acousto-optic mode locker 62 in combination with crystal 54 and aperture 60, as well as the reflection of laser light along optical axis 56 between mirrors 58 and 64 is well known. The result is an output from oscillator 14 which is best characterized as a pulsed laser beam 16.

Figure 3:
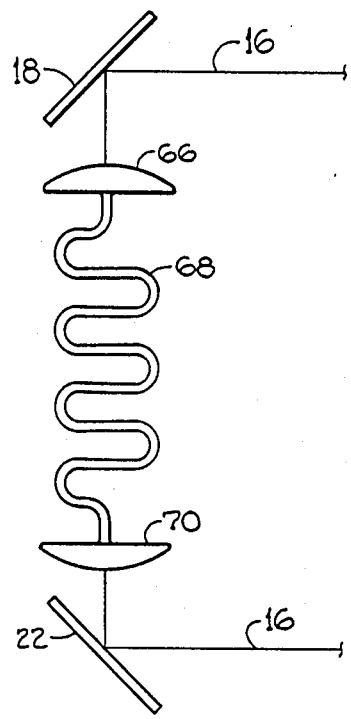
FIG. 3 is a schematic diagram of the line dispersion component of the present invention.

Referring now to FIG. 3, it is seen that the optical connection between oscillator 14 and dispersion line 20 is accomplished by turning mirror 18. Dispersion line 20 comprises an objective lens 66 which focuses beam 16 onto an optical fiber 68. Preferably, optical fiber 68 is a monomode optical fiber approximately 20 meters in length of a type well known in the art. In accordance with the present invention, pulses in beam 16 which are emitted from oscillator 14 pass through optical fiber 68 where, by virtue of the differences in the path length followed by pulses in beam 16 as they pass through optical fiber 68, the wavelengths within each pulse of beam 16 are spread. Once wavelengths in beam 16 have been spread in their passage through optical fiber 68, objective lens 79 refocuses the pulses of beam 16 as they emerge from optical fiber 68. As shown in FIG. 3, pulsed laser beam 16 is then directed from dispersion line 20 into regenerative amplifier 24 by the action of turning mirror 22.

Figure 4:
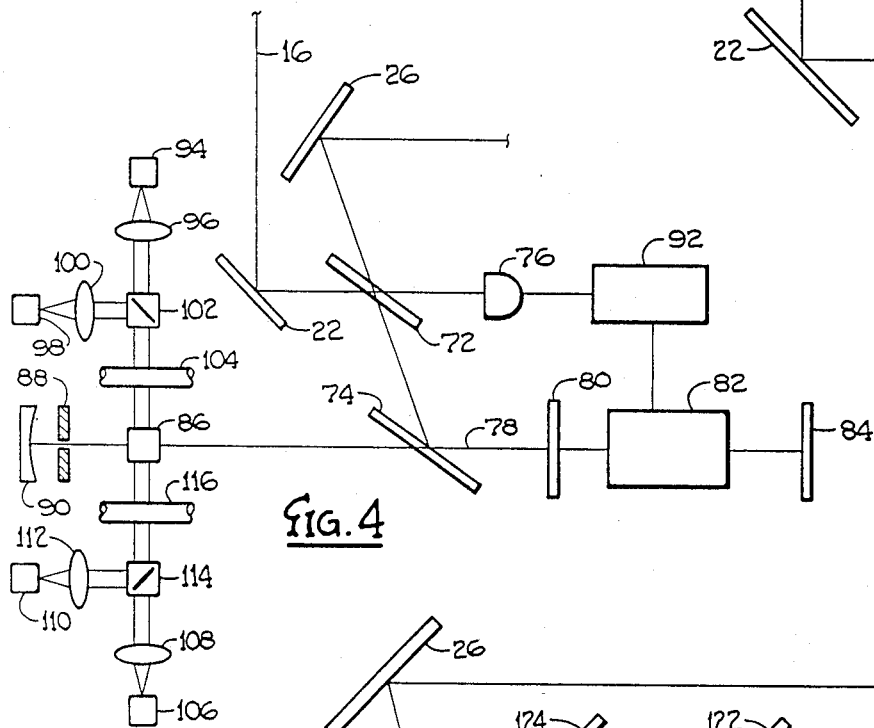
FIG. 4 is a schematic diagram of the regenerative amplifier of the present invention.

In FIG. 4 it will be seen that pulsed laser beam 16, after being reflected by turning mirror 22, is incident upon an uncoated glass beam splitter 72. The uncoated glass beam splitter 72 diverts a portion of laser beam 16 toward polarizing beam splitter 74 and directs the remainder of pulsed laser beam 16 toward photodiode trigger 76. That portion of pulsed laser beam 16 which is diverted by uncoated glass beam splitter 72 toward polarizing beam splitter 74 is polarized by beam splitter 74 and directed along optical path 78. In sequence, pulses of laser beam 16 pass through quarterwave plate 80 and electro-optical crystal 82 and are incident upon a flat 100% mirror 84 where they are reflected back through electro-optical crystal 82 and quarterwave plate 80. It is to be understood that quarterwave plate 80 is of any type well known in the pertinent art and that electro-optical crystal 82 is of the type generally known as a Pockels' cell.

After being reflected by flat 100% mirror 84 through quarterwave plate 80 on optical path 78, the pulse has passed through quarterwave plate 80 twice. This causes the plane of polarization of pulses in laser beam 16 to be rotated a total of 90 degrees. This rotation allows the pulses to pass through polarizing beam splitter 74 and continue along optical path 78 to be successively incident upon crystal 86, pass through aperture 88 and be reflected back through aperture 88 and crystal 86 by curved 100% mirror 90. It will be understood that during this initial passage of beam 16 through regenerative amplifier 24, crystal 82 is not activated. During subsequent passages, however, pulses in laser beam 16 can be confined within regenerative amplifier 24 for reciprocal reflection along optical path 78 depending upon further rotations in polarization imparted to the pulses of laser beam 16 as they pass through electro-optical crystal 82. If electro-optical crystal 82 is activated by electronic switch 92 to rotate each pulse an additional 90 degrees during its two passes through electro-optical crystal 82, both quarterwave plate 80 and crystal 82 will combine their effects to rotate the plane of polarization of each pulse 180 degrees. Thus, each time a pulse is incident on polarizing beam splitter 74, it will pass therethrough and be effectively captured in reflections along optical path 78. Subsequently, in accordance with the predetermined desires of the operator, electronic switch 92 can activate electro-optical crystal 82 to rotate the plane of polarization of each pulse 180 degrees during two excursions of the pulse through electro-optical crystal 82. This rotation by electro-optical crystal 82, in its combined effect with the rotation caused by quarterwave plate 80 brings each pulse of laser beam 16 into a polarization alignment for reflection of the pulse out of optical path 78 by the polarizing beam splitter 74.

In accordance with the above described operation, pulses in laser beam 16 are accepted by regenerative amplifier 24 for reflection along optical path 78. Then, in accordance with the activation of electro-optical crystal 82 to rotate the plane of polarization 90 degrees during the two passages of the pulse through electro-optical crystal 82, the pulses are retained within regenerative amplifier 24 for reflection back and forth along optical path 78 between flat 100% mirror 84 and curved 100% mirror 90. Subsequent activation of electro-optical crystal 82 into a state which imparts a 180 degree rotation to the polarization of light in the pulses will cause reflection of the amplified pulse out of optical path 78 by polarizing beam splitter 74.

FIG. 4 also shows that pulsed laser beam 16, as it passes along optical path 78, is influenced by a pumping chamber similar to the pumping chamber used in cooperation with oscillator 14. Within this pumping chamber, laser diode 94 directs its light through collimating lens 96 and laser diode 98 directs its light through collimating lens 100. Light from laser diodes 94 and 98 are combined at beam splitter 102 and directed through cylindrical lens 104. Likewise, laser diode 106 in cooperation with a collimating lens 108 and laser diode 110 in cooperation with collimating lens 112 pass collimated light through beam splitter 114 and direct it through cylindrical lens 116. Light from both cylindrical lens 104 and 116 are then directed to be incident upon crystal 86 in a manner similar to the discussion above relative to crystal 54. Preferably, crystal 86, like crystal 54, is a YSGG:Cr:Nd:Er.

FIG. 4 also schematically shows the location of photodiode trigger 76 and electronic switch 92 relative to the electro-optical crystal 82. It is to be understood that the portion of each pulse in laser beam 16 which passes through uncoated glass beam splitter 72 is incident upon photodiode trigger 76 which can be timed to sequentially activate electronic switch 92. Electronic switch 92, in turn, activates electro-optical crystal 82 into the polarizing regime necessary to capture a pulse of laser beam 16 on optical path 78 and keep it there during the time required for amplification of the pulses in beam 16. Crystal 82 is also activated by electrical switch 92 to the level which, in accordance with the previous disclosure, polarizes pulses for reflection by beam splitter 74 out of optical path 78. FIG. 4 also shows that when pulses of laser beam 16 are reflected out of optical path 78, they pass through uncoated glass beam splitter 72 and are incident on turning mirror 26 for further radiation toward pulse compressor 28.

Figure 5:
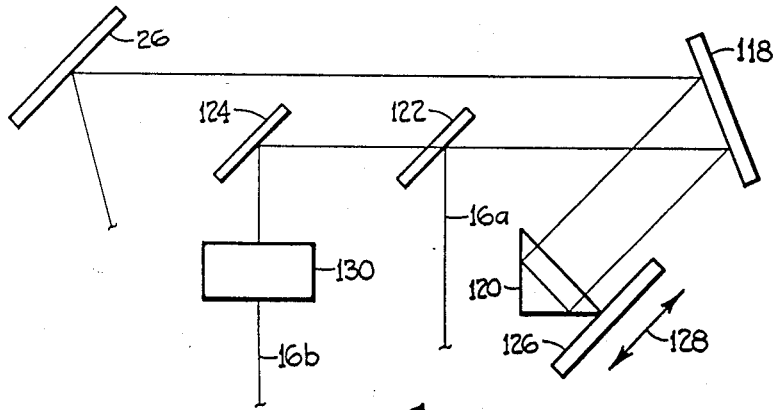
FIG. 5 is a schematic diagram of the pulse compressor of the present invention.

FIG. 5 shows that, after reflection from turning mirror 26, laser beam 16 is incident upon grating 118. After its interaction with grating 118, laser beam 16 is further reflected toward corner cube 120 where it is reflected along an offset path back to grating 118. From grating 118, laser beam 16 is incident on 50% mirror 122 which reflects half of beam 16 as a separate laser beam 16a having a predetermined wavelength. The 50% of laser beam 16 which passes through 50% mirror 122 is incident on 100% mirror 124 and directed toward a frequency doubler 130.

It will be appreciated by the skilled artisan that the duration of each pulse in beam 16 can be controlled by selecting the distance at which corner cube 120 is placed from grating 118. For this purpose, a rail 126 is provided in operative association with corner cube 120 for movement of corner cube 120 in the directions indicated by arrow 128. It will be further appreciated by the skilled artisan that movement of corner cube 120 in the directions indicated by arrow 128 will cause determinable changes in the duration by each pulse in laser beam 16. More specifically, a position change of 45 centimeters by corner cube 120 will cause a duration change in each pulse from 40 picoseconds to 1 picosecond.

After reflection from 50% mirror 122, laser beam 16a is placed into operation in accordance with the desires of the operator. Likewise, that portion of laser beam 16 which passes through 50% mirror 122, for incidence upon 100% mirror 124, is reflected by 100% mirror 124 and into a frequency doubler 130. Consequently, the wavelength of light in each pulse of laser beam 16 emerging from frequency doubler 130 is half the wavelength of the light which is directed toward frequency doubler 130. The result is that laser beam 16b, having half the wavelength of laser beam 16a, is provided for use in accordance with the desires of the operator. Specifically, each pulse generated by the laser source 10 will contain a visible component of approximately 1.06 micron wavelength which can be passed through frequency doubler 130 to establish another component having a wavelength of approximately 0.532 microns. These are components of visible light which are effective for internal ablation procedures. Also, laser source 20 simultaneously produces a component of light having a wavelength of approximately 2.94 microns. This is an infrared component which is useful for external ablation. It follows that once these components are generated, means for selectively focusing the desired component is employed in cooperation with laser source 10.

While the particular multiwavelength laser source as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

We claim:

1. A laser apparatus which comprises:
    an oscillator optically pumped by a laser diode for establishing a beam comprising a plurality of pulses of monochromatic light;
    a dispersion line for spreading wavelengths in said pulses and being optically connected to said oscillator to receive said pulses;
    a regenerative amplifier for amplifying said pulses and being optically connected to said dispersion line; and
    a pulse compressor optically connected to said regenerative amplifier for establishing a pulse duration for said beam.

2. A laser apparatus as cited in claim 1 comprising a plurality of laser diodes for pumping said oscillator, each of said laser diodes being optically connected to said oscillator.

3. A laser apparatus as cited in claim 2 wherein said oscillator comprises an acousto-optic mode locker for generating said pulses.

4. A laser apparatus as cited in claim 3 wherein said regenerative amplifier comprises means for establishing a repetition rate for said pulses.

5. A laser apparatus as cited in claim 4 wherein said pulse compressor comprises means for varying the duration of each of said pulses received by said means.

6. A laser apparatus as cited in claim 5 wherein said means for establishing a repetition rate for said pulses is an electro-optical crystal.

7. A laser apparatus as cited in claim 6 wherein said means for varying pulse duration comprises a grating and a corner cube moveable relative to said grating to establish the pulse duration.

8. A laser apparatus as cited in claim 7 further comprising a frequency doubler optically connected to said pulse compressor to provide a plurality of pulsed laser beams.

9. A laser apparatus as cited in claim 8 wherein said dispersion line is a monomode optical fiber.

10. A multiwavelength laser apparatus which comprises:
    means including an active medium for originating a beam of light-frequency radiation pulses having a plurality of discrete wavelengths;
    means for spreading the wavelengths of said light-frequency radiation pulses, said spreading means optically connected to said originating means;
    means for setting the repetition rate of said light-frequency radiation pulses, said setting means being optically connected to said spreading means; and
    means for establishing the duration of each of said pulses, said duration establishing means being optically connected to said setting means such that a laser beam of compressed pulses is generated.

11. A laser apparatus as cited in claim 10 wherein said originating means is an oscillator.

12. A laser apparatus as cited in claim 11 wherein said spreading means is a dispersion line.

13. A laser apparatus as cited in claim 12 wherein said setting means is a regenerative amplifier.

14. A laser apparatus as cited in claim 13 wherein said establishing means is a pulse compressor.

15. A laser apparatus as cited in claim 14 wherein said oscillator comprises a YSGG:Cr:Nd:Er crystal for simultaneously lasing light with an infrared wavelength component and a visible wavelength component.

16. A laser apparatus as cited in claim 15 wherein said originating means comprises an array of laser diodes and an acousto-optic mode locker.

17. A laser apparatus as cited in claim 16 wherein said setting means comprises an electro-optical crystal.

18. A laser apparatus as cited in claim 17 further comprising a frequency doubler for halving the wavelengths of said light-frequency radiation pulses.

19. A laser apparatus as cited in claim 18 further comprising means to select said visible wavelength component for internal ablation and select said infrared wavelength component for external ablation.

20. a method for generating a laser beam of compressed pulses which comprises the steps of:

(A) Directing monochromatic light through a mode locker to generate a beam of light-frequency radiation pulses;

(B) Spreading the wavelengths of the light within each of said pulses for subsequent compression thereof;

(C) Setting the repetition rate of said light-frequency radiation pulses to reduce the quiescent interval between said pulses; and (D) Compressing said beam by establishing the duration of each of said light-frequency radiation pulses.

21. A method for creating a laser beam as cited in claim 20 wherein said repetition rate is greater than ten thousand pulses per second.

22. A method for creating a laser beam as cited in claim 20 wherein the duration of said light-frequency radiation pulses is less than forty picoseconds.

* * * * *